(12) United States Patent
Cho et al.

(10) Patent No.: US 11,058,790 B2
(45) Date of Patent: Jul. 13, 2021

(54) ELECTRONIC APPARATUS HAVING PHOTOCATALYTIC FILTER

(71) Applicant: SAMSUNG ELECTRONICS CO., LTD., Suwon-si (KR)

(72) Inventors: Hong Kwan Cho, Suwon-si (KR); Jee Yong Kim, Suwon-si (KR); Ah Hyun Bae, Hwaseong-si (KR); Myung Ju Shin, Suwon-si (KR); Il Yong Cho, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 526 days.

(21) Appl. No.: 15/878,029

(22) Filed: Jan. 23, 2018

(65) Prior Publication Data

US 2018/0207311 A1 Jul. 26, 2018

(30) Foreign Application Priority Data

Jan. 24, 2017 (KR) .................. 10-2017-0010898

(51) Int. Cl.
*A61L 9/20* (2006.01)
*B01D 53/88* (2006.01)
(Continued)

(52) U.S. Cl.
CPC .......... *A61L 9/205* (2013.01); *B01D 53/8687* (2013.01); *B01D 53/8696* (2013.01);
(Continued)

(58) Field of Classification Search
CPC .. A61L 9/205; A61L 2209/11; A61L 2209/14; F24F 11/70; F24F 8/10; B01D 53/8687; B01D 53/8696; B01D 53/885
See application file for complete search history.

(56) References Cited

U.S. PATENT DOCUMENTS

| 2002/0037240 A1 | 3/2002 | Okada et al. |
| 2008/0050272 A1 | 2/2008 | Carey |
| 2019/0263226 A1* | 8/2019 | Gruenbeck .......... B01D 53/885 |

FOREIGN PATENT DOCUMENTS

| CN | 1330254 A | 1/2002 |
| CN | 2633628 Y | 8/2004 |

(Continued)

OTHER PUBLICATIONS

European Search Report dated Dec. 12, 2019 in related European Application No. 19180501.9.

(Continued)

*Primary Examiner* — Sean E Conley
(74) *Attorney, Agent, or Firm* — Staas & Halsey LLP

(57) ABSTRACT

An electronic apparatus capable of controlling the air purification performance of a photocatalytic filter according to an air volume of a blowing fan and a concentration of a specific gas. An electronic apparatus having a deodorizing performance recovery function of a photocatalytic filter. The electronic apparatus includes a blowing fan, a filter apparatus configured to purify air introduced by the blowing fan and a controller configured to adjust a current applied to the filter apparatus, wherein the filter apparatus comprises a light emitting module to which a plurality of light emitting portions configured to output ultraviolet light is mounted, a photocatalytic filter provided to face the light emitting portion and a support frame configured to support the light emitting module and the photocatalytic filter to be apart from each other by a predetermined distance.

13 Claims, 14 Drawing Sheets

(51) Int. Cl.
    *B01D 53/86*    (2006.01)
    *F24F 11/70*    (2018.01)
    *F24F 8/10*    (2021.01)
    *F24F 110/50*    (2018.01)
    *F24F 8/22*    (2021.01)
    *F24F 8/167*    (2021.01)

(52) U.S. Cl.
    CPC .............. *B01D 53/885* (2013.01); *F24F 8/10* (2021.01); *F24F 11/70* (2018.01); *A61L 2209/11* (2013.01); *A61L 2209/14* (2013.01); *B01D 2255/2073* (2013.01); *B01D 2255/20707* (2013.01); *B01D 2255/20776* (2013.01); *B01D 2255/20792* (2013.01); *B01D 2255/802* (2013.01); *B01D 2257/708* (2013.01); *B01D 2257/90* (2013.01); *B01D 2257/91* (2013.01); *B01D 2258/06* (2013.01); *B01D 2259/4508* (2013.01); *B01D 2259/804* (2013.01); *F24F 8/167* (2021.01); *F24F 8/22* (2021.01); *F24F 2110/50* (2018.01)

(56) References Cited

FOREIGN PATENT DOCUMENTS

| | | |
|---|---|---|
| CN | 101370579 A | 2/2009 |
| CN | 101371929 A | 2/2009 |
| CN | 101790389 | 7/2010 |
| CN | 203829870 U | 9/2014 |
| DE | 10 2016 117 797 A1 | 12/2016 |
| EP | 0826531 A2 | 3/1998 |
| JP | 9-309329 | 12/1997 |
| JP | 2001-79069 | 3/2001 |
| KR | 10-2006-0017572 | 2/2006 |
| KR | 10-2008-0100047 | 11/2008 |
| KR | 10-2012-0105703 | 9/2012 |
| WO | WO 2008/144519 A1 | 11/2008 |
| WO | 2009/096924 A1 | 8/2009 |
| WO | 2010/109796 A1 | 9/2010 |
| WO | WO 2015/139606 A1 | 9/2015 |

OTHER PUBLICATIONS

Database WPI, Week 199807, Thomson Scientific, London, GB; AN 1998-071378, XP002782117, Dec. 2, 1997.
Chinese Office Action dated Nov. 22, 2019 in related Chinese Application No. 201810067589.5.
European Office Action dated Apr. 11, 2019 in corresponding European Patent Application No. 18152775.5 (4 pages).
Extended European Search Report dated Oct. 22, 2018 in corresponding European Patent Application No. 18152775.5.
Database WPI, Week 199807, Thomson Scientific, London, GB; AN 1998-071378 XP002782117 & JP H09 309329 A, Dec. 2, 1997, 2 pgs.
Chinese Office Action dated Aug. 10, 2020 in Chinese Patent Application No. 201810067589.5.
Chinese Office Action dated Feb. 2, 2021 in Chinese Patent Application No. 201810067589.5.

* cited by examiner

ELECTRONIC APPARATUS HAVING PHOTOCATALYTIC FILTER

CROSS-REFERENCE TO RELATED APPLICATION(S)

This application is based on and claims priority under 35 U.S.C. § 119 to Korean Patent Application No. 10-2017-0010898, filed on Jan. 24, 2017 in the Korean Intellectual Property Office, the disclosure of which is incorporated by reference herein in its entirety.

BACKGROUND

1. Field

Embodiments of the present disclosure relate to an electronic apparatus such as an air conditioning apparatus, an air cleaner, or a ventilator having a photocatalytic filter.

2. Description of Related Art

Electronic apparatuses for sucking and discharging outside air such as an air conditioning apparatus, an air cleaner or a ventilator include a filter configured to remove particles or harmful gas which generate malodor.

Among the filters, photocatalytic filters provide excellent sterilization and deodorizing effect through photochemical reaction of photocatalyst and ultraviolet light. The photocatalytic filter generates hydroxyl radical and oxide ions to oxidize volatile organic compounds and to remove microorganisms adsorbed to the surface of the photocatalyst.

The photocatalyst can be used semi-permanently and can be operated stably without harming human body.

SUMMARY

Therefore, it is an aspect of the present disclosure to provide an electronic apparatus capable of controlling the air purification performance of a photocatalytic filter according to an air volume of a blowing fan or a concentration of a specific gas.

It is another aspect of the present disclosure to provide an electronic apparatus having a deodorizing performance recovery function of a photocatalytic filter.

Additional aspects of the present disclosure will be set forth in part in the description which follows and, in part, will be obvious from the description, or may be learned by practice of the present disclosure.

In accordance with one aspect of the present disclosure, an electronic apparatus includes: a blowing fan, a filter apparatus configured to purify air introduced by the blowing fan and a controller configured to adjust a current applied to the filter apparatus, wherein the filter apparatus comprises a light emitting module to which a plurality of light emitting portions configured to output ultraviolet light is mounted, a photocatalytic filter provided to face the light emitting portion and a support frame configured to support the light emitting module and the photocatalytic filter to be apart from each other by a predetermined distance.

The controller may adjust a current applied to the light emitting portion by corresponding to a strength of an air volume of the blowing fan.

When the strength of the air volume of the blowing fan is changed to a second mode, which is stronger than a first mode, the controller may increase a current value, which is applied to the light emitting portion, to a second current value, which is greater than a first current value corresponding to the first mode.

When the strength of the air volume of the blowing fan is changed to the first mode, which is weaker than the second mode, the controller may decrease a current value, which is applied to the light emitting portion, to the first current value, which is less than the second current value corresponding to the second mode.

An electronic apparatus may further includes: a gas sensor configured to detect a predetermined gas contained in the air introduced by the blowing fan.

The controller may adjust a current applied to the light emitting portion by corresponding to a concentration of the gas detected by the gas sensor.

When the concentration of the gas detected by the gas sensor is greater than a first reference concentration, the controller may increase a current value applied to the light emitting portion, to be greater than a reference current value corresponding to the reference concentration.

When the concentration of the gas detected by the gas sensor is less than the first reference concentration, the controller may decrease a current value applied to the light emitting portion, to be less than the reference current value corresponding to the reference concentration.

In a state in which the concentration of the gas is greater than a second reference concentration or a cumulative concentration of the gas is greater than a third reference concentration, when the blowing fan is operated, the controller may stop the drive of the blowing fan and operates the light emitting portion for a predetermined period of time so that ultraviolet light is irradiated to the photocatalytic filter.

In a state in which a command to recover a deodorizing performance is input, when the blowing fan is operated, the controller may stop the drive of the blowing fan and operates the light emitting portion for a predetermined period of time so that ultraviolet light is irradiated to the photocatalytic filter.

When the drive of blowing fan is stopped, the controller may operate the light emitting portion for a predetermined period of time so that ultraviolet light is irradiated to the photocatalytic filter in order to recover the deodorizing performance of the photocatalytic filter.

In a state in which a clean air delivery rate (CADR) of the electronic apparatus reaches a reference value, when the blowing fan is operated, the controller may stop the drive of the blowing fan and operates the light emitting portion for a predetermined period of time so that ultraviolet light is irradiated to the photocatalytic filter to recover the deodorizing performance of the photocatalytic filter.

When the blowing fan is operated for equal to or greater than a predetermined driving time, the controller may stop the drive of the blowing fan and operates the light emitting portion for a predetermined period of time so that ultraviolet light is irradiated to the photocatalytic filter to recover the deodorizing performance of the photocatalytic filter.

The photocatalytic filter may include a base a photocatalyst applied to the base.

In accordance with another aspect of the present disclosure, a control method of an electronic apparatus includes: when a blowing fan is operated, determining a strength of an air volume of the blowing fan, adjusting a current applied to a light emitting portion according to the strength of the air volume of the blowing fan and when the drive of the blowing fan is stopped, operating the light emitting portion for a predetermined period of time so that ultraviolet light is irradiated to a photocatalytic filter.

The adjustment of the current applied to the light emitting portion according to the strength of the air volume of the blowing fan may include: when the strength of the air volume of the blowing fan is changed to a second mode, which is stronger than a first mode, increasing a current value, which is applied to the light emitting portion, to a second current value, which is greater than a first current value corresponding to the first mode and when the strength of the air volume of the blowing fan is changed to the first mode, which is weaker than the second mode, decreasing a current value, which is applied to the light emitting portion, to the first current value, which is less than the second current value corresponding to the second mode.

The adjustment of the current applied to the light emitting portion according to the strength of the air volume of the blowing fan may include: when a concentration of a gas detected by a gas sensor is greater than a first reference concentration, increasing a current value applied to the light emitting portion, to be greater than a reference current value corresponding to a reference concentration and when the concentration of the gas detected by the gas sensor is less than the first reference concentration, decreasing a current value applied to the light emitting portion, to be less than the reference current value corresponding to the reference concentration.

When the drive of the blowing fan is stopped, operating the light emitting portion for a predetermined period of time so that ultraviolet light is irradiated to a photocatalytic filter, may include: in a state in which a clean air delivery rate (CADR) of the electronic apparatus reaches a reference value, when the blowing fan is operated, stopping the drive of the blowing fan; and operating the light emitting portion for the predetermined period of time so that ultraviolet light is irradiated to the photocatalytic filter to recover the deodorizing performance of the photocatalytic filter.

When the drive of the blowing fan is stopped, operating the light emitting portion for a predetermined period of time so that ultraviolet light is irradiated to a photocatalytic filter, may include: when the blowing fan is operated for equal to or greater than a predetermined driving time, stopping the drive of the blowing fan; and operating the light emitting portion for the predetermined period of time so that ultraviolet light is irradiated to the photocatalytic filter to recover the deodorizing performance of the photocatalytic filter.

When the drive of the blowing fan is stopped, operating the light emitting portion for a predetermined period of time so that ultraviolet light is irradiated to a photocatalytic filter, may include in a state in which the concentration of the gas is greater than a second reference concentration or a cumulative concentration of the gas is greater than a third reference concentration, when the blowing fan is operated, stopping the drive of the blowing fan and operating the light emitting portion for the predetermined period of time so that ultraviolet light is irradiated to the photocatalytic filter.

BRIEF DESCRIPTION OF THE DRAWINGS

These and/or other aspects of the disclosure will become apparent and more readily appreciated from the following description of embodiments, taken in conjunction with the accompanying drawings of which.

DETAILED DESCRIPTION

Figure 1:
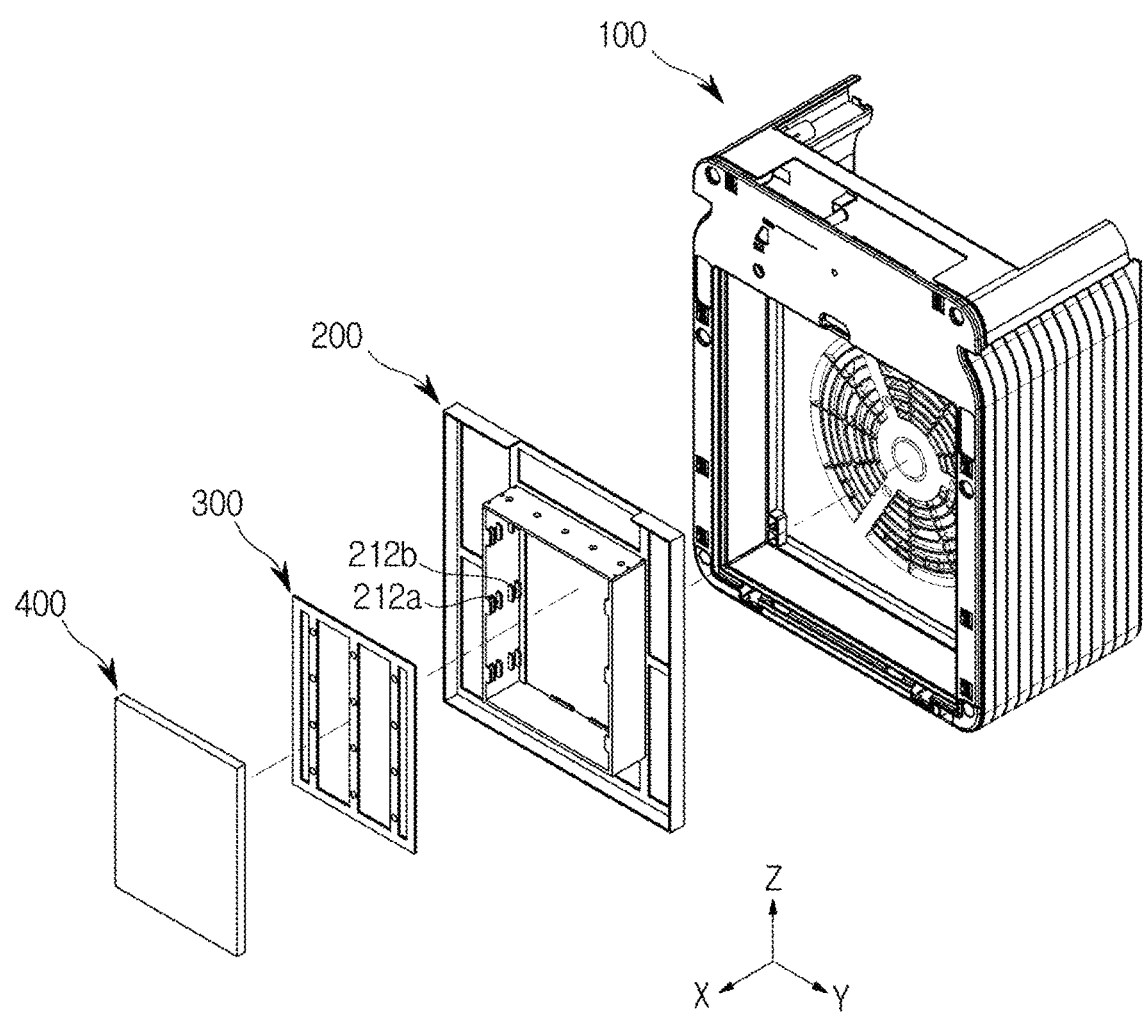
FIGS. 1 and 2 are views illustrating a filter apparatus and a blowing fan of an electronic apparatus in accordance with an embodiment.

Embodiments described in the present disclosure and configurations shown in the drawings are merely examples of the embodiments of the present disclosure, and may be modified in various different ways at the time of filing of the present application to replace the embodiments and drawings of the present disclosure.

Also, the terms used herein are used to describe the embodiments and are not intended to limit and/or restrict the present disclosure.

The singular forms "a," "an" and "the" are intended to include the plural forms as well, unless the context clearly indicates otherwise.

In this present disclosure, the terms "including", "having", and the like are used to specify features, numbers, steps, operations, elements, components, or combinations thereof, but do not preclude the presence or addition of one or more of the features, elements, steps, operations, elements, components, or combinations thereof.

It will be understood that, although the terms first, second, third, etc., may be used herein to describe various elements, but elements are not limited by these terms. These terms are only used to distinguish one element from another element.

In the following description, terms such as "part", "unit", "block", "member", and "module" indicate a unit for processing at least one function or operation, wherein the unit and the block may be embodied as software or hardware, such as Field Programmable Gate Array (FPGA), Application Specific Integrated Circuit (ASIC), or embodied by combining hardware and software.

In addition, the same reference numerals or signs shown in the drawings of the present disclosure indicate elements or components performing substantially the same function.

Figure 2:
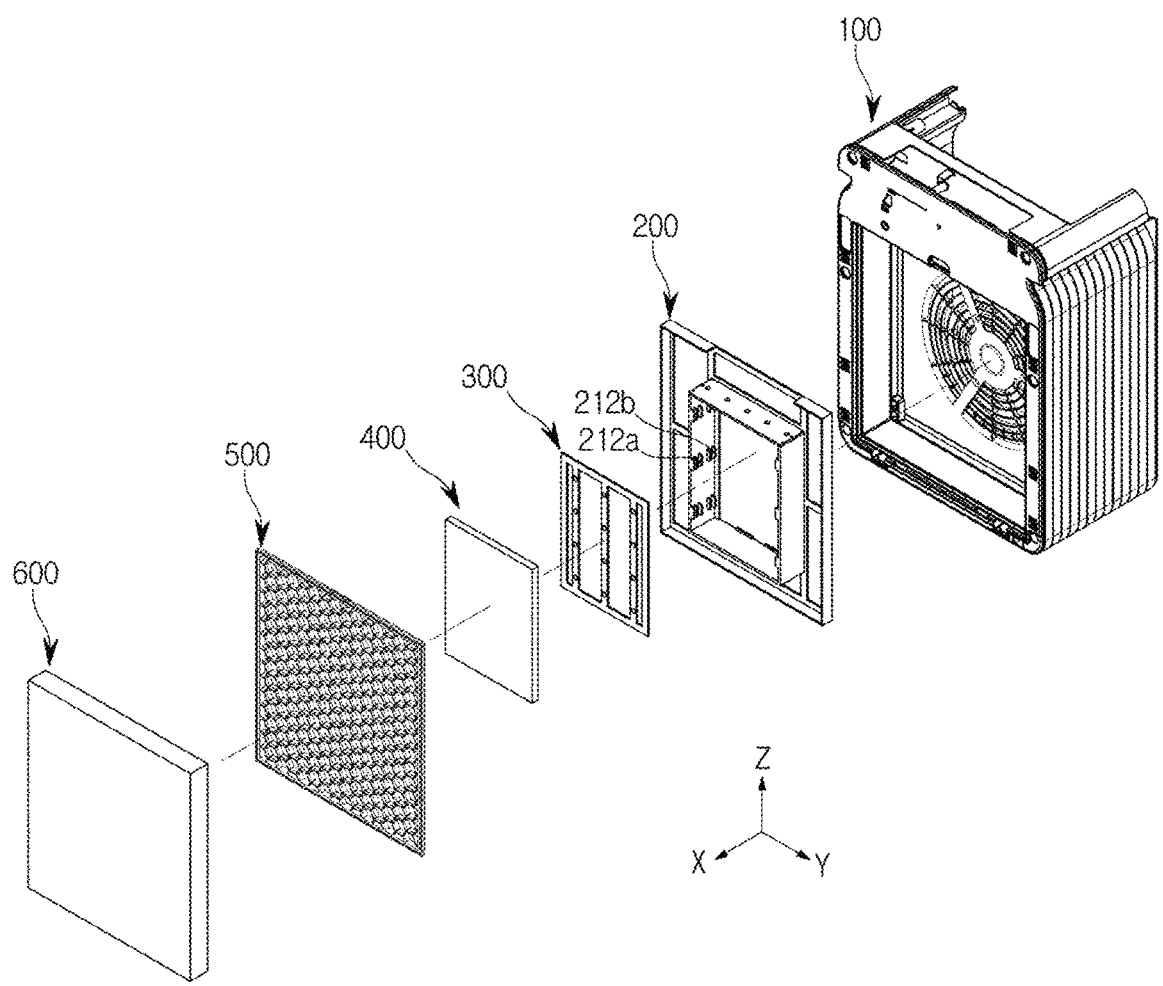
Figure 3:
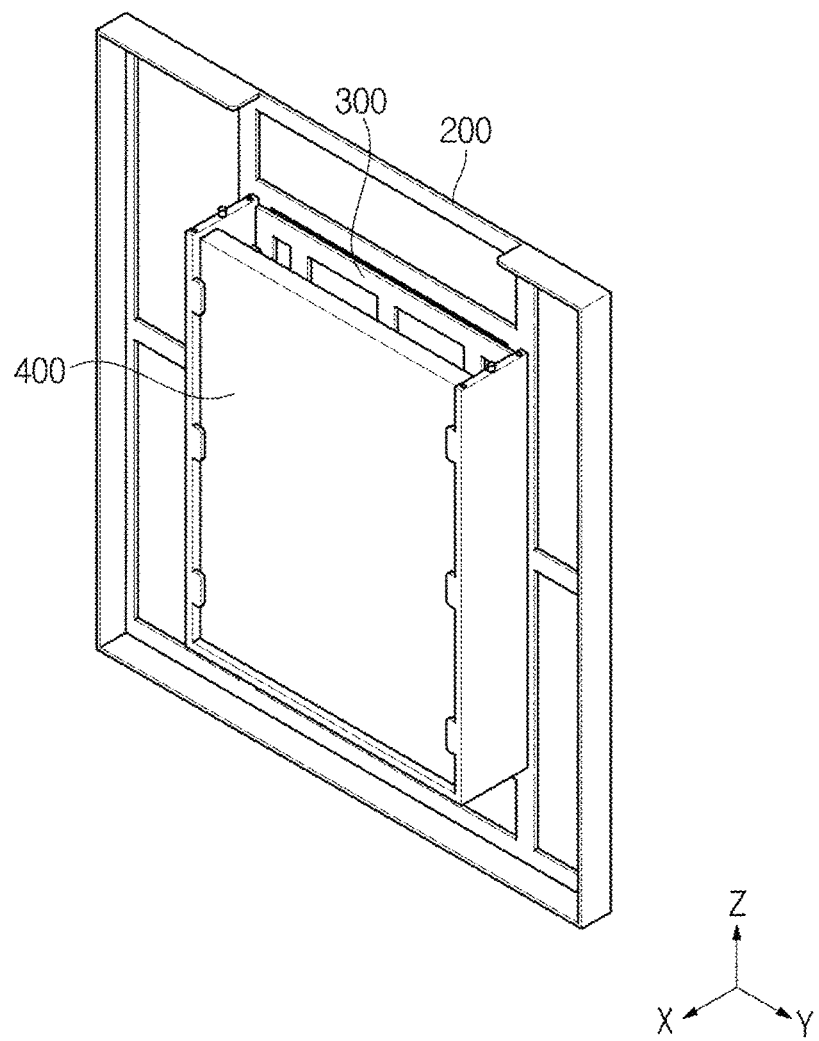
FIG. 3 is a view illustrating an assembly of the filter apparatus of FIG. 1.
Figure 4:
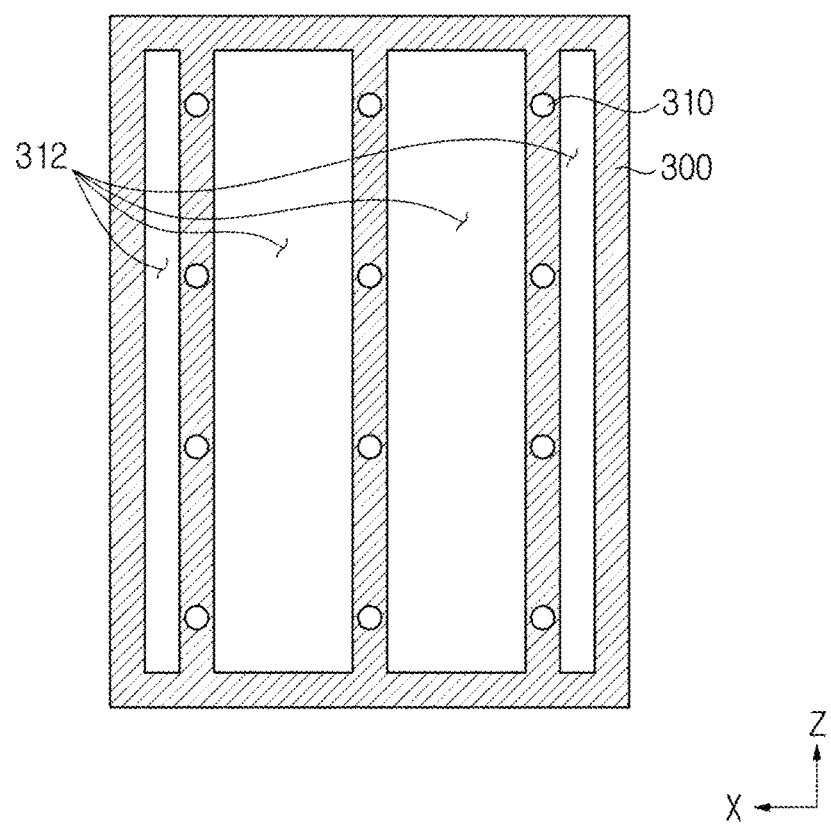
FIG. 4 is a view illustrating a light emitting module of the electronic apparatus in accordance with an embodiment.
Figure 5:
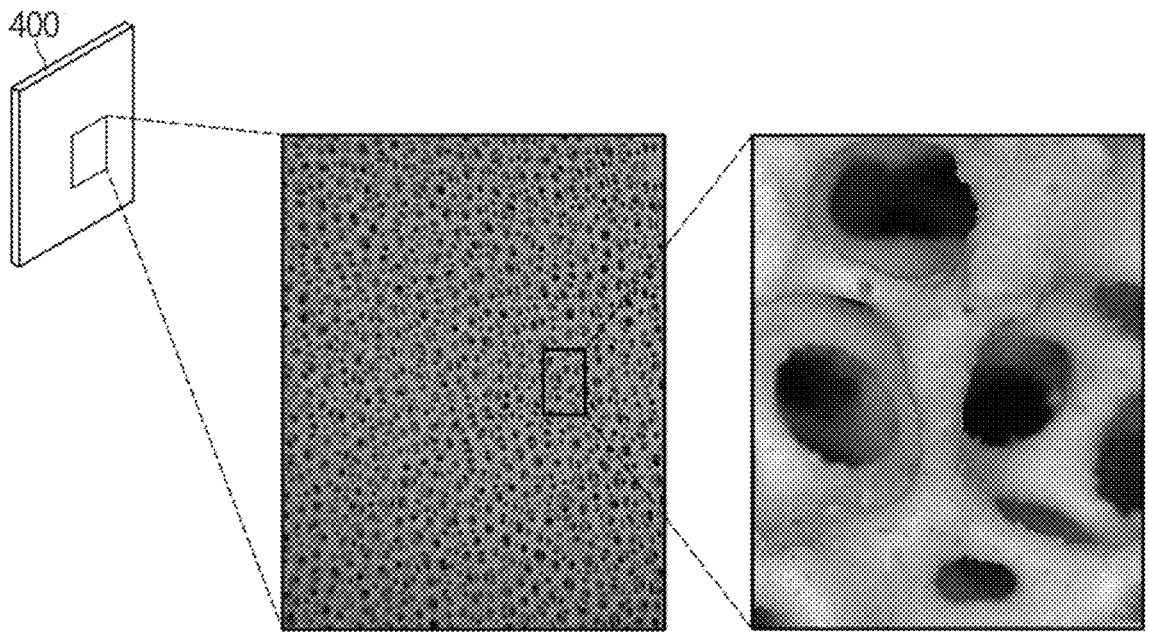
FIGS. 5 and 6 are enlarged-views illustrating a photocatalytic filter of the electronic apparatus in accordance with an embodiment.
Figure 6:
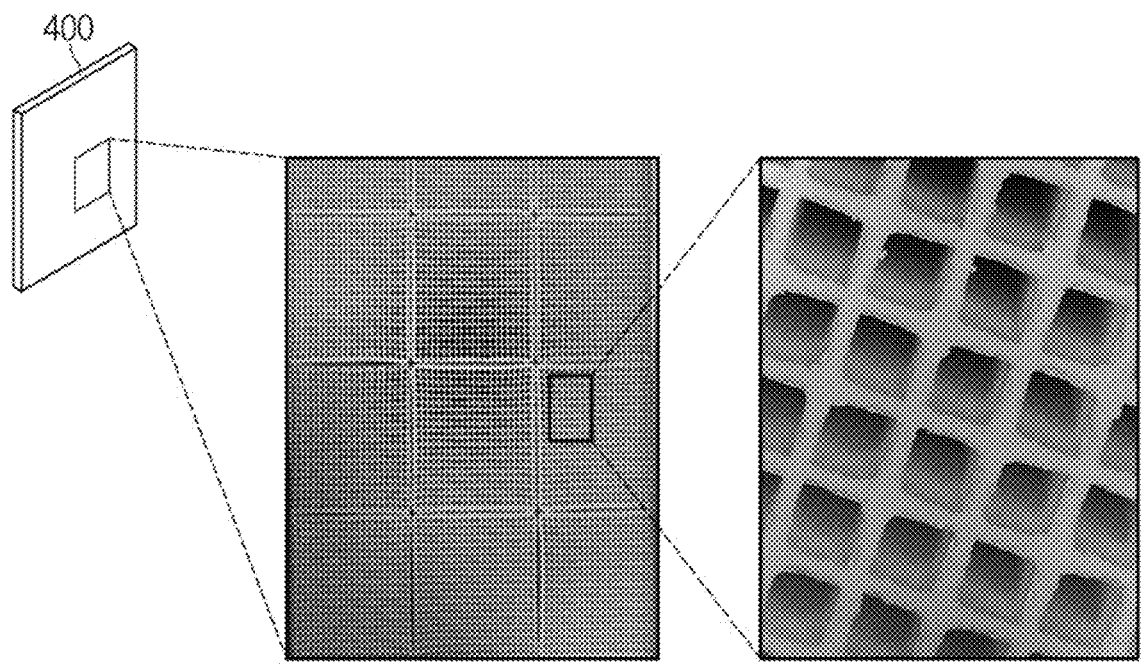

FIGS. 1 and 2 are views illustrating a filter apparatus and a blowing fan of an electronic apparatus in accordance with an embodiment, and FIG. 3 is a view illustrating an assembly of the filter apparatus of FIG. 1. FIG. 4 is a view illustrating a light emitting module 300 of the electronic apparatus in accordance with an embodiment, and FIGS. 5 and 6 are enlarged-views illustrating a photocatalytic filter of the electronic apparatus in accordance with an embodiment.

According to the disclosed embodiment, an electronic apparatus is an electronic apparatus provided with a blowing fan 100 and a filter apparatus, and includes an apparatus configured to generate the air flow by suctioning and discharging the outside air, such as an air conditioning apparatus, an air cleaner or a ventilator.

Referring to FIG. 1, according to an embodiment, the electronic apparatus may include the blowing fan 100 configured to suction the outside air, and the filter apparatus configured to purify the outside air suctioned by the blowing fan 100.

The filter apparatus may include a light emitting module 300 to which a plurality of light emitting portions 310 configured to emit ultraviolet light, is mounted, a photocatalytic filter 400 provided to face the light emitting portion 310, and a support frame 200 configured to support the light emitting module 300 and the photocatalytic filter 400 so that the light emitting module 300 and the photocatalytic filter 400 are apart from each other by a predetermined distance.

The photocatalytic filter 400 may include a base and photocatalyst applied to the base. As illustrated in FIG. 5, the base may be implemented as a foam type plate including an atypical hole. Alternatively, the base of the photocatalytic filter 400 may be implemented as a honey-comb shaped plate. The shape of the photocatalytic filter 400 as illustrated in FIGS. 5 and 6 is merely an example, and thus the shape of the photocatalytic filter 400 is not limited thereto.

According to the disclosed embodiment, the base of the photocatalytic filter 400 may be formed of a ceramic material. For example, the base of the photocatalytic filter 400 may be formed of a cordierite or a mullite composed of alumina and silica, or formed of a combination of cordierite and mullite.

As illustrated in FIGS. 5 and 6, the photocatalytic filter 400 is implemented by applying a photocatalyst to the above mentioned base, and according to the disclosed embodiment, the photocatalyst may include at least one of titanium dioxide, tungsten trioxide, manganese dioxide, zinc oxide, and titanium tetraisopropoxide.

The photocatalyst may be applied to the base by a spray method or by an impregnation method.

As for the titanium dioxide, when ultraviolet light is irradiated, electrons in the valence band are excited and move to the conduction band, and holes are generated in the valence band. In a state in which the titanium dioxide has band gap energy of 3.2 eV, when ultraviolet light is irradiated, energy greater than the band gap energy is absorbed, and thus the electrons are excited and holes are generated, as mentioned above.

When the electrons and the holes are reacted with oxygen and water, oxide ions and hydroxyl radicals may be generated, and the oxide ions and the hydroxyl radicals may purify the suctioned outside air by chemically decomposing and oxidizing various bacteria, viruses, and organic compounds. The photocatalyst may purify the outside air by removing organic chlorine compounds, volatile hydrocarbons, aldehydes, ketones, alcohols, phenols, ammonia, hydrogen sulfide, nitrogen oxides and sulfur oxides.

The light emitting module 300 may include the light emitting portion 310 configured to emit ultraviolet light and a support portion in which the light emitting portion 310 is installed.

The light emitting module 310 may be implemented as a UV-LED configured to emit ultraviolet light of a UV-A wavelength band (315 nm~400 nm). The light emitting portion 310 may emit ultraviolet light having a wavelength band of 360 nm~370 nm as the primary wavelength range, and may be provided to have an irradiation angle of 110 degree or more.

As illustrated in FIG. 4, the light emitting portion 310 may be installed apart from the support portion by a predetermined distance, and the distance between the light emitting portion 310, the number of the light emitting portion 310, and the arrangement of the light emitting portion 310 may be determined based on an irradiation angle of the light emitting portion 310 and a distance from the photocatalytic filter 400.

The support portion of the light emitting module 300 may be provided in a thickness of approximately 1 mm~2 mm, and formed of aluminum or a heat-dissipating material. As illustrated in FIG. 4, as for the support portion of the light emitting module 300, a hole 312 configured to allow the outside air, introduced by the blowing fan 100, to pass through, may be formed except a portion in which the light emitting portion 310 is installed and an outer frame.

The support frame 200 configured to support the photocatalytic filter 400 and the light emitting module 300 may include a groove 212a, and 212b configured to allow the photocatalytic filter 400 and the light emitting module 300 to be apart from each other. The groove of the support frame 200 may be provided to allow a distance between the photocatalytic filter 400 and the light emitting module 300 to be approximately 15 mm-25 mm.

As illustrated in FIG. 3, the photocatalytic filter 400 and the light emitting module 300 may be mounted to each groove of the support frame 200 so that the photocatalytic filter 400 and the light emitting module 300 are apart from each other.

As illustrated in FIG. 2, according to another embodiment, an electronic apparatus may further include at least one of a deodorizing filter 500 and a dust filter 600, as well as the photocatalytic filter 400. As illustrated in FIG. 2, the dust filter 600 and the deodorizing filter 500 may be provided in front of the photocatalytic filter 400.

The dust filter 600 may include a pre-filter, a high efficiency particulate (HEPA) filter, and an electrostatic precipitator, and the deodorizing filter 500 may include a carbon filter, but the dust filter 600 and the deodorizing filter 500 are not limited thereto. Therefore, the dust filter 600 and the deodorizing filter 500 may be implemented by well-known various filters.

Figure 7:
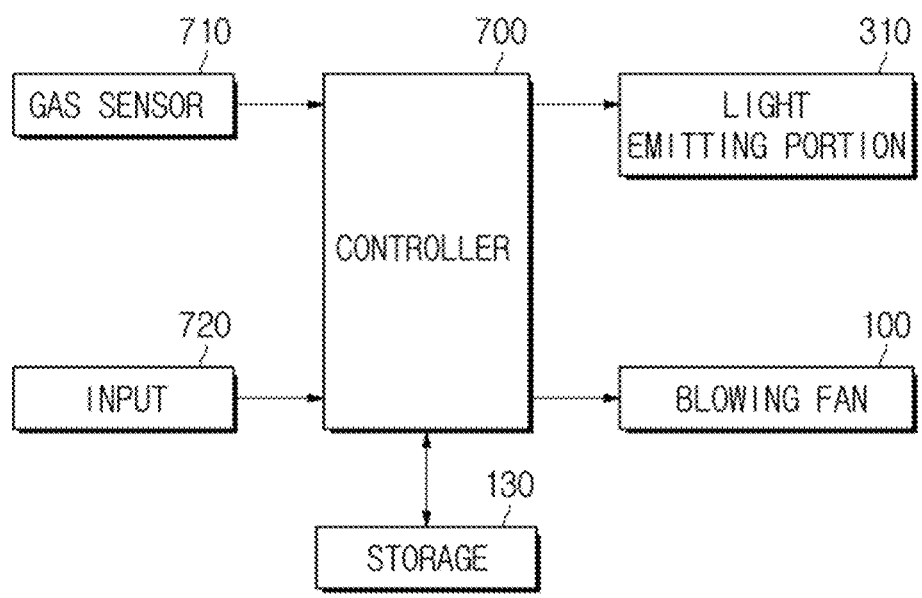
FIG. 7 is a view illustrating a configuration of the electronic apparatus in accordance with an embodiment.
Figure 8:
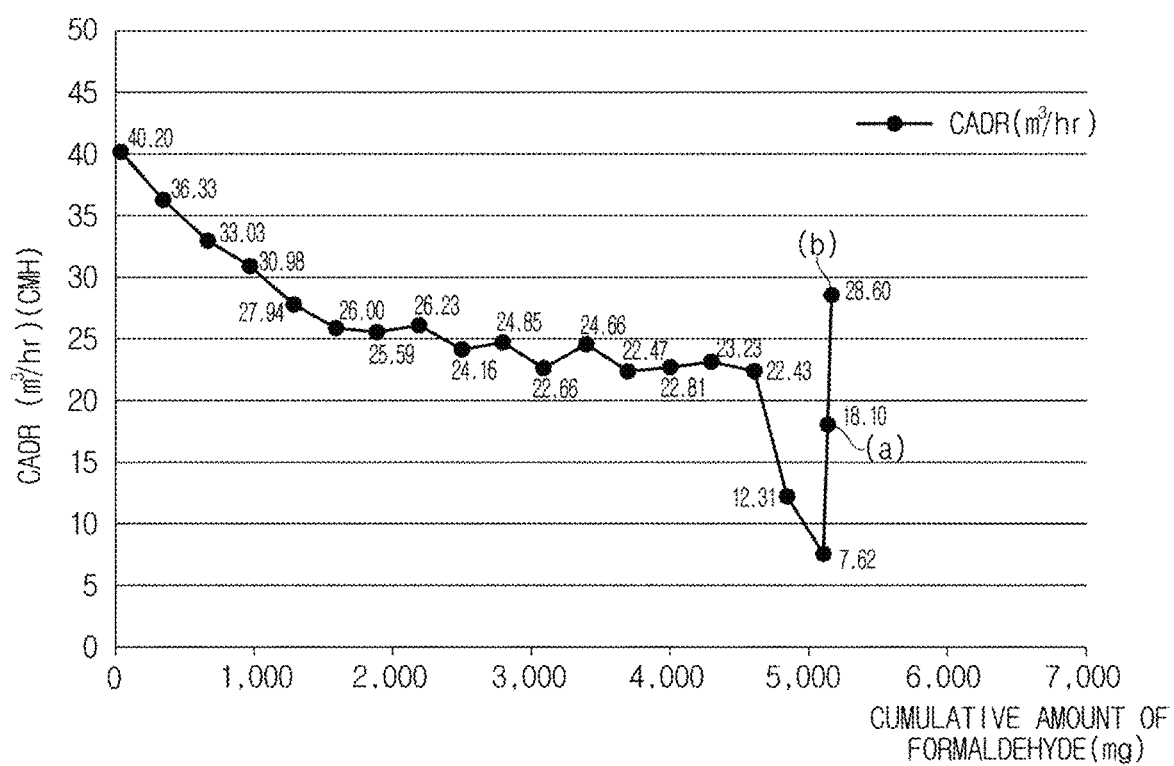
FIG. 8 is a graph illustrating a change in the performance of the photocatalytic filter of the electronic apparatus in accordance with an embodiment.

FIG. 7 is a view illustrating a configuration of the electronic apparatus in accordance with an embodiment, and FIG. 8 is a graph illustrating a change in the performance of the photocatalytic filter 400 of the electronic apparatus in accordance with an embodiment.

As illustrated in FIG. 7, according to an embodiment, the electronic apparatus may include a gas sensor 710 configured to detect the concentration of a certain gas, an input 720 configured to receive a command related to the operation of the electronic apparatus, a light emitting portion 310 configured to irradiate ultraviolet light to the photocatalytic filter 400, and a blowing fan 100 configured to introduce the outside air.

The gas sensor 710 may be configured to detect a certain gas such as formaldehyde, and may be implemented by a semiconductor type gas sensor, a contact combustion type sensor and an electrochemical sensor.

The semiconductor type gas sensor may measure a concentration of a gas by measuring the influence of the change of the resistance component as the measurement target material is oxidized or reduced. The electrochemical type gas sensor may measure a concentration of a gas by measuring the amount of ions generated by oxidizing/reducing the gas dissolved in the electrolyte.

The gas sensor 710 may employ various well-known gas sensors. Since the gas detected by the gas sensor 710 is not limited to formaldehyde, a gas sensor configured to detect a variety of gas may be provided and a plurality of gas sensors configured to detect different gas may be provided.

The gas sensor 710 may be installed around the blowing fan 100 or the filer apparatus to detect gas contained in the outside air introduced by the blowing fan 100. Alternatively, the plurality of gas sensors 710 may be installed in a different position around the blowing fan 100 or the filter apparatus.

The gas sensor 710 transmits data about the concentration of the detected gas to the controller 700.

The input 720 may be configured to receive a command to adjust the air volume of the blowing fan 100, and configured to receive a command to recover the deodorizing performance of the photocatalytic filter 400 described later. The input 720 may include a plurality of input tools configured to receive a variety of command related to the operation of the electronic apparatus, e.g., a button, a joystick, a jog shuttle, a touch panel, a voice input device, a motion recognition device, and a remote controller.

A storage 130 may store control programs and control data for the control of the operation of the electronic apparatus and various application programs and application data to perform various functions according to the user input.

For example, the storage 130 may store an operating system (OS) program for managing the configuration and the resources (hardware and software) included in the electronic apparatus.

The storage 130 may include a non-volatile memory in which data is not lost although the power is turned off. For example, the storage 130 may include a large-capacity flash memory or a solid state drive (SSD).

The controller 700 may control the drive of the blowing fan 100 or the light emitting portion 310 based on a command to adjust the air volume of the blowing fan 100, a command to recover the deodorizing performance, which are input through the input 720, or data about the concentration of the gas detected by the gas sensor 710.

The controller 700 may control the light emitting portion 310 and the blowing fan 100 contained in the electronic apparatus, according to the user input, which is received through the input 720, the concentration of the gas, which is detected by the gas sensor 710, and/or programs and data stored in the storage 130.

The controller 700 may include a micro-processor configured to perform the calculation to control the electronic apparatus, and a memory to store/memorize the programs and data related to the calculation operation of the microprocessor.

The microprocessor may call the data stored/memorized in the memory according to the program stored/memorized in the memory, and perform the arithmetic or logic operation on the called data. In addition, the microprocessor may output the result of arithmetic or logic operations, to the memory.

The memory may include a volatile memory in which the stored data is lost when the power is turned off. The volatile memory may call programs and data from the above mentioned storage 130, and temporarily store the called data. The volatile memory may provide the stored programs and data to the microprocessor, and restore data, which is output from the microprocessor. The volatile may include a Static Random Access Memory (S-RAM) and a Dynamic Random Access Memory (D-RAM).

As needed, the memory may include a non-volatile memory in which data is not lost although the power is turned off. The non-volatile memory may store a firmware to manage and initiate components contained in the electronic apparatus. The non-volatile memory may include a Read Only Memory (ROM), an Erasable Programmable Read Only memory (EPROM), and an Electrically Erasable Programmable Read Only memory (EEPROM), and a flash memory.

It has described that the microprocessor and the memory are functionally separated from each other, but it is not required that the microprocessor and the memory are physically separated from each other. For example, the microprocessor and the memory may be implemented by a single chip or by a separate chip.

As mentioned above, the controller 700 may control the entire operation of the electronic apparatus and it is assumed that the operation of the electronic apparatus described later is controlled by the controller 700.

Hereinbefore it has described that the controller 700 and the storage 130 are functionally separated from each other, but it is not required that the controller 700 and the storage 130 are physically separated from each other. For example, the controller 700 and the storage 130 may be implemented by a single chip or by a separate chip.

According to an embodiment, the electronic apparatus may adjust the performance of the photocatalytic filter 400 by controlling a current value applied to the light emitting portion 310 according to the change in the air volume of the blowing fan 100.

For example, the controller 700 may increase a current value applied to the light emitting portion 310, when a command to change the air volume of the blowing fan 100 from a first mode to a second mode, i.e., a command to increase the air volume of the blowing fan 100, is input.

The first mode and the second mode may be a relative concept, which is that the first mode is an air volume of the blowing fan 100 weaker than a second mode, and the second mode is an air volume of the blowing fan 100 stronger than the first mode. For example, when the first mode is a weak mode, the second mode may be a moderate mode or a strong mode, and when the first mode is a moderate mode, the second mode may be a strong mode. In the same manner, when the second mode is a strong mode, the first mode may be a weak mode or a moderate mode, and when the second mode is a moderate mode, the first mode may be a weak mode.

When a command to change the first mode to the second mode is input, the controller 700 may increase a first current value, which is applied to the light emitting portion 310 by corresponding to the first mode, to a second current value, which is applied to the light emitting portion 310 by corresponding to the second mode. For example, the controller 700 may apply the first current value of 100 mA to the light emitting portion 310 in the first mode and when the mode is changed from the first mode to the second mode, the controller 700 may apply the second current value of 300 mA to the light emitting portion 310, which is increased from 100 mA.

When the air volume of the blowing fan 100 is increased, the amount of outside air, which is introduced per a reference time, may be increased and thus it may be difficult to secure the air purification performance of the photocatalytic filter 400, which is required to correspond to the increased air volume of the outside air, by using the intensity of the ultraviolet light, which is irradiated to the photocatalytic filter 400 before the air volume is increased.

Therefore, when the air volume of the blowing fan 100 is increased, the intensity of the ultraviolet light, which is irradiated to the photocatalytic filter 400 from the light emitting portion 310, may be needed to be increased to increase the air purification performance of the photocatalytic filter 400. According to an embodiment, when a mode change command to increase the air volume of the blowing fan 100, is input, the controller 700 may increase the air purification performance of the photocatalytic filter 400 by increasing the current value applied to the light emitting portion 310.

In addition, when the command to change the air volume of the blowing fan 100 from the second mode to the first mode is input via the input 720, i.e., a command to reduce the air volume of the blowing fan 100 is input, the controller 700 may reduce the current value applied to the light emitting portion 310.

When a command to change the second mode to the first mode is input, the controller 700 may decrease the second current value, which is applied to the light emitting portion 310 by corresponding to the second mode, to the first current value, which is applied to the light emitting portion 310 by corresponding to the first mode. For example, in a state in which the controller 700 applies the second current value of 300 mA to the light emitting portion 310, when the mode is changed from the second mode to the first mode, the controller 700 may apply the first current value of 100 mA to the light emitting portion 310, which is reduced from 300 mA.

When the air volume of the blowing fan 100 is decreased, the amount of outside air, which is introduced per a reference time, may be decreased and thus the intensity of ultraviolet light, which is irradiated to the photocatalytic filter 400 before the air volume is reduced, may provide a unnecessarily high air purification performance in comparison with the air purification performance of the photocatalytic filter 400 corresponding to the reduced amount of the outside air. It may lead to the waste of the power.

Therefore, when the air volume of the blowing fan 100 is decreased, the intensity of the ultraviolet light, which is irradiated to the photocatalytic filter 400 from the light emitting portion 310, may be needed to be decreased to reduce the air purification performance of the photocatalytic filter 400. According to an embodiment, when a mode change command to decrease the air volume of the blowing fan 100, is input, the controller 700 may decrease the air purification performance of the photocatalytic filter 400 by reducing the current value applied to the light emitting portion 310.

As mentioned above, according to an embodiment, the electronic apparatus may adjust the air purification performance of the photocatalytic filter 400 in a variable manner by adjusting the current value, which is applied to the light emitting portion 310, according to the variation of the air volume of the blowing fan 100.

According to the disclosed embodiment, when the concentration of a certain gas detected by the gas sensor 710, is increased, the electronic apparatus may control the current value applied to the light emitting portion 310 to adjust the performance of the photocatalytic filter 400.

For example, when the concentration of formaldehyde detected by the gas sensor 710 is equal to or greater than a first reference concentration, the controller 700 may increase the current value applied to the light emitting portion 310. The formaldehyde is merely an example and thus another gas may become a target gas to be detected.

That is, when the detected concentration of formaldehyde is equal to or greater than the first reference concentration, the controller 700 may determine that a stronger air purification performance is required, and thus the controller 700 may apply a current value, which is increased higher than a reference current value corresponding to the first reference concentration, so that the intensity of ultraviolet light irradiated to the photocatalytic filter 400 is increased.

When the detected concentration of formaldehyde is reduced less than the first reference concentration, the controller 700 may determine that a situation in which the strong air purification performance is required, is released, and the controller 700 may apply a current value, which is reduced less than the reference current value corresponding to the first reference concentration, so that the intensity of ultraviolet light irradiated to the photocatalytic filter 400 is reduced.

The above mentioned first reference concentration may be a certain concentration value of formaldehyde, but is not limited thereto. Therefore, the first reference concentration may mean a certain range of formaldehyde concentration. In a state in which the first reference concentration represents a certain range of formaldehyde concentration, when a gas concentration equal to or greater than the upper limit of the range is detected or when a gas concentration equal to or less than the lower limit of the range is detected, a current value, which is applied to the light emitting portion 310 may be increased equal to or greater than the reference current value in accordance with the upper limit of the range, or the current value, which is applied to the light emitting portion 310 may be decreased equal to or greater than the reference current value in accordance with the lower limit of the range.

As mentioned above, according to an embodiment, the electronic apparatus may adjust the air purification performance of the photocatalytic filter 400 in a variable manner by adjusting the current value, which is applied to the light emitting portion 310, according to the variation of the concentration of a certain gas detected by the gas sensor 710.

According to the disclosed embodiment, the electronic apparatus may recover the air purification performance of the photocatalytic filter 400, i.e., the deodorizing and sterilizing performance. That is, when a condition, which is to determine whether the photocatalytic filter 400 is contaminated, is satisfied, the controller 700 of the electronic apparatus may perform a control to recover the air purification performance of the photocatalytic filter 400.

For example, when a command to recover the deodorizing performance is input via the input 720, the controller 700 may determine whether the blowing fan 100 is operated or not. When the blowing fan 100 is operated, the controller 700 may stop the drive of the blowing fan 100, and operate the light emitting portion 310 for the predetermined period of time, so that ultraviolet light is irradiated to the photocatalytic filter 400 for the predetermined period of time. When the blowing fan 100 is not operated, the controller 700 may immediately operate the light emitting portion 310 for the predetermined period of time.

When the command to recover the deodorizing performance is input by a user, the controller 700 may determine whether the blowing fan 100 is operated or not. In a state in which the blowing fan 100 is operated, when ultraviolet light is irradiated to the photocatalytic filter 400, it may be similar with a case in which the deodorization and sterilization are performed by the photocatalytic filter 400. Therefore, the controller 700 may determine whether the blowing fan 100 is operated or not.

In a state in which the flow of the outside air by the blowing fan 100 is stopped, when ultraviolet light is irradiated to the photocatalytic filter 400, contaminants attached to the photocatalytic filter 400 may be decomposed or removed by the reaction of the photocatalyst with ultraviolet light, and thus the deodorizing and sterilizing performance of the photocatalytic filter 400 may be restored.

The input 720 may be implemented to allow a user to select a recovery time of the deodorizing performance when the user inputs the command for the deodorizing performance recovery. For example, the input 720 may include an input tool configured to receive a command for the deodorizing performance recovery for 15 minutes, and an input tool configured to receive a command for the deodorizing performance recovery for 1 hour. Alternatively, the input 720 may include an input tool configured to receive a command for the deodorizing performance recovery, and an input tool configured to receive a time for the deodorizing performance recovery.

In other words, a period of time, in which the light emitting portion 310 is operated for the deodorizing performance recovery, may be determined by the input 720. When an additional input related to a period of time is not performed, the light emitting portion 310 may be driven for a predetermined period of time.

Although the deodorizing performance recovery command is not input via the input 720, the controller 700 may automatically perform the control for the deodorizing performance recovery when an amount of clean air is reduced equal to or less than a reference value. The amount of clean air may be illustrated by clean air delivery rate (CADR) indicating the volume of air that is purified each time, and the unit thereof may be indicated by $m^3/h$.

In other words, when clean air delivery rate (CADR) is reduced equal to or less than the reference value, the controller 700 may determine whether the blowing fan 100 is operated or not. When the blowing fan 100 is operated, the controller 700 may stop the drive of the blowing fan 100, and operate the light emitting portion 310 for the predetermined period of time, so that ultraviolet light is irradiated to the photocatalytic filter 400 for the predetermined period of time. When the blowing fan 100 is not operated, the controller 700 may immediately operate the light emitting portion 310 for the predetermined period of time. A current value, which is applied to the light emitting portion 310 when the light emitting portion 310 is operated for the predetermined period of time, may be pre-determined and the controller 700 may apply the predetermined and stored current value to the light emitting portion 310.

When the clean air delivery rate (CADR) is reduced equal or less than the reference value, the controller 700 may determine whether the blowing fan 100 is operated or not. In a state in which the blowing fan 100 is operated, when ultraviolet light is irradiated to the photocatalytic filter 400, it may be similar with a case in which the deodorization and sterilization are performed by the photocatalytic filter 400. Therefore, the controller 700 may determine whether the blowing fan 100 is operated or not.

In a state in which the flow of the outside air by the blowing fan 100 is stopped, when ultraviolet light is irradiated to the photocatalytic filter 400, contaminants attached to the photocatalytic filter 400 may be decomposed or removed by the reaction of the photocatalyst with ultraviolet light, and thus the deodorizing and sterilizing performance of the photocatalytic filter 400 may be restored.

Although the deodorizing performance recovery command is not input via the above mentioned input 720, the controller 700 may automatically perform the control for the deodorizing performance recovery when a driving time of the blowing fan 100 is equal to or greater than a predetermined driving time. The driving time of the blowing fan 100 may be a cumulative driving time.

That is, when a cumulative driving time of the controller 700 is equal to or greater than the predetermined drive time, e.g., 10 hours, the controller 700 may determine whether the blowing fan 100 is operated. The cumulative driving time may exceed 10 hours during the blowing fan 100 is operated, or the drive of the blowing fan 100 may be stopped since the electronic apparatus is stopped shortly after the cumulative driving time exceeds 10 hours, and thus the controller 700 may determine whether the blowing fan 100 is operated or not.

When the blowing fan 100 is operated, the controller 700 may stop the drive of the blowing fan 100, and operate the light emitting portion 310 for the predetermined period of time, so that ultraviolet light is irradiated to the photocatalytic filter 400 for the predetermined period of time. When the blowing fan 100 is not operated, the controller 700 may immediately operate the light emitting portion 310 for the predetermined period of time. A current value, which is applied to the light emitting portion 310 when the light emitting portion 310 is operated for the predetermined period of time, may be pre-determined, and the controller 700 may apply the predetermined and stored current value to the light emitting portion 310.

In a state in which the flow of the outside air by the blowing fan 100 is stopped, when ultraviolet light is irradiated to the photocatalytic filter 400, contaminants attached to the photocatalytic filter 400 may be decomposed or removed by the reaction of the photocatalyst with ultraviolet light, and thus the deodorizing and sterilizing performance of the photocatalytic filter 400 may be restored.

Although the deodorizing performance recovery command is not input via the input 720, the controller 700 may automatically perform the control for the deodorizing performance recovery when a concentration of the certain gas detected by the gas sensor 710 is higher than a second reference concentration or when a concentration of the certain gas detected by the gas sensor 710 is higher than a third reference concentration. The above mentioned first to third reference concentration corresponding to a reference value, which is compared with the concentration of the certain gas, may be pre-stored in the storage 130 or the memory. The first to third reference concentrations may be determined by the test and stored in advance, and may have different values. Alternatively, the first to third reference concentrations may be set as a value desired by the user and then stored.

For example, when a concentration of formaldehyde detected by the gas sensor 710 is equal to or higher than the second reference concentration or when a cumulative concentration of formaldehyde detected by the gas sensor 710 is equal to or higher than the third reference concentration, the controller 700 may determine whether the blowing fan 100 is operated or not.

When the blowing fan 100 is operated, the controller 700 may stop the drive of the blowing fan 100, and operate the light emitting portion 310 for the predetermined period of time, so that ultraviolet light is irradiated to the photocatalytic filter 400 for the predetermined period of time. When the blowing fan 100 is not operated, the controller 700 may immediately operate the light emitting portion 310 for the predetermined period of time. A current value, which is applied to the light emitting portion 310 when the light emitting portion 310 is operated for the predetermined period of time, may be pre-determined and the controller 700 may apply the predetermined and stored current value to the light emitting portion 310.

In a state in which the flow of the outside air by the blowing fan 100 is stopped, when ultraviolet light is irradiated to the photocatalytic filter 400, contaminants attached to the photocatalytic filter 400 may be decomposed or removed by the reaction of the photocatalyst with ultraviolet light, and thus the deodorizing and sterilizing performance of the photocatalytic filter 400 may be restored.

Table 1 illustrates a clean air delivery rate (CADR) of an air cleaner provided with the photocatalytic filter 400 according to the disclosed embodiment and a clean air delivery rate (CADR) of an air cleaner provided with a carbon filter in a conventional manner Data shown in the table was acquired under the same condition except for the difference in a deodorizing filter, wherein the photocatalytic filter 400 is used for one case and the carbon filter is used for the other case.

TABLE 1

| Formaldehyde cumulative amount (mg) | A | B |
|---|---|---|
| 0 | 40 m$^3$/h | 40 m$^3$/h |
| 600 | 34 m$^3$/h | 34 m$^3$/h |
| 1200 | 27 m$^3$/h | 28 m$^3$/h |
| 1800 | 20 m$^3$/h | 26 m$^3$/h |
| 2400 | 15 m$^3$/h | 24 m$^3$/h |
| 3000 | 12 m$^3$/h | 23 m$^3$/h |
| 3600 | 4 m$^3$/h | 22 m$^3$/h |
| 4200 | — | 23 m$^3$/h |
| 4800 | — | 22 m$^3$/h |

A life prediction test according to CCM method of China GBT standard has been applied and it was confirmed that the air cleaner, to which the photocatalytic filter 400 according to the disclosed embodiment is applied, has a dominant position in terms of the clean air delivery rate (CADR), as the cumulative amount of formaldehyde is increased.

FIG. 8 is a graph illustrating a change in the performance of the photocatalytic filter 400 of the electronic apparatus in accordance with an embodiment. In FIG. 8, a horizontal axis illustrates the cumulative amount of formaldehyde and a vertical axis illustrates the clean air delivery rate (CADR).

Referring to FIG. 8, an initial clean air delivery rate (CADR) of the photocatalytic filter 400 has 40 m$^3$/h and the clean air delivery rate (CADR) of the photocatalytic filter 400 has approximately 22 m$^3$/h in a range of the cumulative amount of formaldehyde of approximately 2000 mg~4500 mg.

In order to confirm the effect of the deodorizing performance recovery of the photocatalytic filter 400 according to the disclosed embodiment, the clean air delivery rate (CADR) is reduced to approximately 7 m$^3$/h and then the light emitting portion 310 is operated for 15 minutes or 10 hours in a state in which the blowing fan 100 is stopped.

When the light emitting portion 310 is operated for 15 minutes, the clean air delivery rate (CADR) is increased to approximately 18 m$^3$/h ('a' in FIG. 8). In addition, when the light emitting portion 310 is operated for 10 hours, the clean air delivery rate (CADR) is increased to approximately 29 m$^3$/h ('b' in FIG. 8).

According to the disclosed embodiment, the photocatalytic filter 400 may be semi-permanently used by the function of the deodorizing performance recovery, as illustrated in FIG. 8.

FIGS. 9 to 14 are flowcharts illustrating a control method of the electronic apparatus in accordance with an embodiment. Hereinafter the control method of the electronic apparatus will be described with reference to FIGS. 9 to 14.

Figure 9:
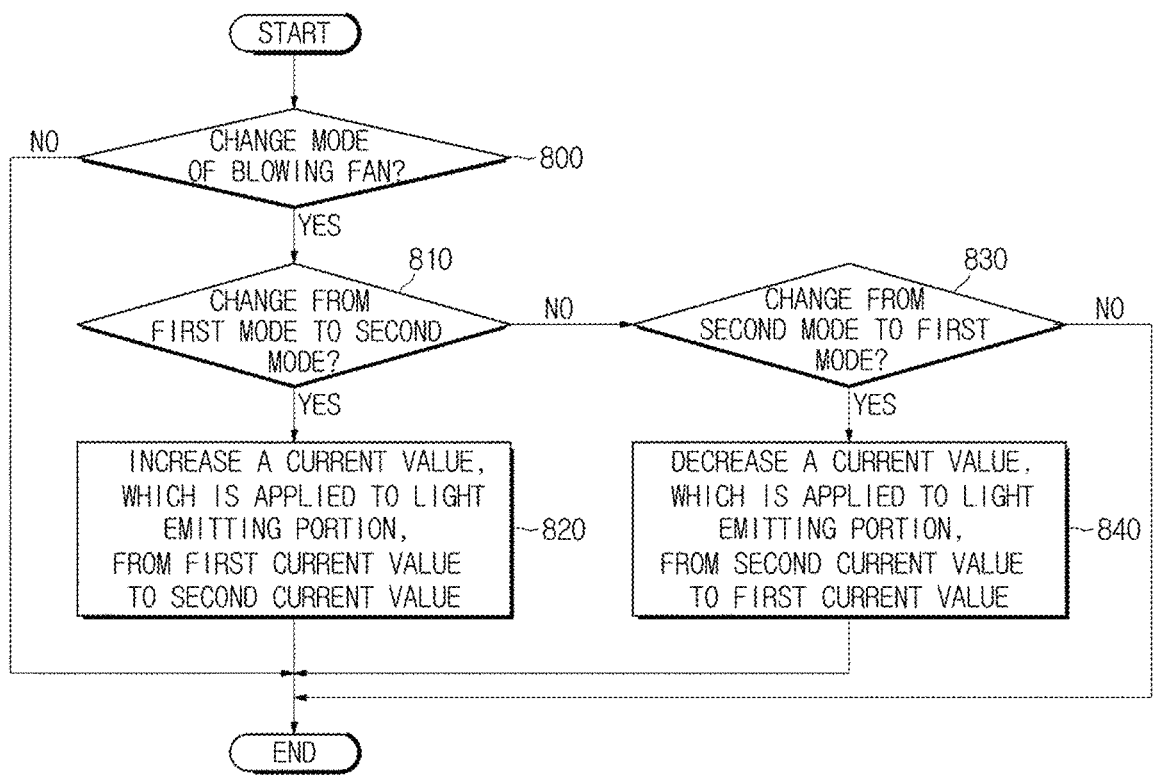
FIGS. 9 to 14 are flowcharts illustrating a control method of the electronic apparatus in accordance with an embodiment.

Referring to FIG. 9, when a mode of the blowing fan 100 is changed from the first mode to the second mode (800 and 810), the controller 700 may increase a current value, which is applied to the light emitting portion 310, from the first current value to the second current value (820).

When the command to change the first mode to the second mode is input, the controller 700 may increase the first current value, which is applied to the light emitting portion 310 by corresponding to the first mode, to the second current value, which is applied to the light emitting portion 310 by corresponding to the second mode. For example, in a state in which the controller 700 applies the first current value of 100 mA to the light emitting portion 310 in the first mode, when the mode is changed from the first mode to the second mode, the controller 700 may apply the second current value of 300 mA to the light emitting portion 310, which is increased from 100 mA.

When the air volume of the blowing fan 100 is increased, the amount of outside air, which is introduced per the reference time, may be increased and thus it may be difficult to secure the air purification performance of the photocatalytic filter 400, which is required to correspond to the increased air volume of the outside air, by using the intensity of the ultraviolet light, which is irradiated to the photocatalytic filter 400 before the air volume is increased. When the air volume of the blowing fan 100 is increased, it may be required that the intensity of ultraviolet light, which is irradiated to the photocatalytic filter 400, is increased to improve the air purification performance of the photocatalytic filter 400. According to an embodiment, when the mode change command to increase the air volume of the blowing fan 100, is input, the controller 700 may increase the air purification performance of the photocatalytic filter 400 by increasing the current value applied to the light emitting portion 310.

When the mode of the blowing fan 100 is changed from the second mode to the first mode (830), the controller 700 may decrease the current value, which is applied to the light emitting portion 310, from the second current value to the first current value (840).

When the command to change the second mode to the first mode is input, the controller 700 may decrease the second current value, which is applied to the light emitting portion 310 by corresponding to the second mode, to the first current value, which is applied to the light emitting portion 310 by corresponding to the first mode. For example, in a state in which the controller 700 applies the second current value of 300 mA to the light emitting portion 310, when the mode is changed from the second mode to the first mode, the controller 700 may apply the first current value of 100 mA to the light emitting portion 310, which is reduced from 300 mA.

When the air volume of the blowing fan 100 is decreased, the amount of outside air, which is introduced per the reference time, may be decreased and thus the intensity of ultraviolet light, which is irradiated to the photocatalytic filter 400 before the air volume is reduced, may provide a unnecessarily high air purification performance in comparison with the air purification performance of the photocatalytic filter 400 corresponding to the reduced amount of the outside air. It may lead to the waste of the power.

Therefore, when the air volume of the blowing fan 100 is decreased, the intensity of the ultraviolet light, which is irradiated to the photocatalytic filter 400 from the light emitting portion 310, may be needed to be decreased to reduce the air purification performance of the photocatalytic filter 400. According to an embodiment, when the mode change command to decrease the air volume of the blowing fan 100, is input, the controller 700 may decrease the air purification performance of the photocatalytic filter 400 by reducing the current value applied to the light emitting portion 310.

Figure 10:
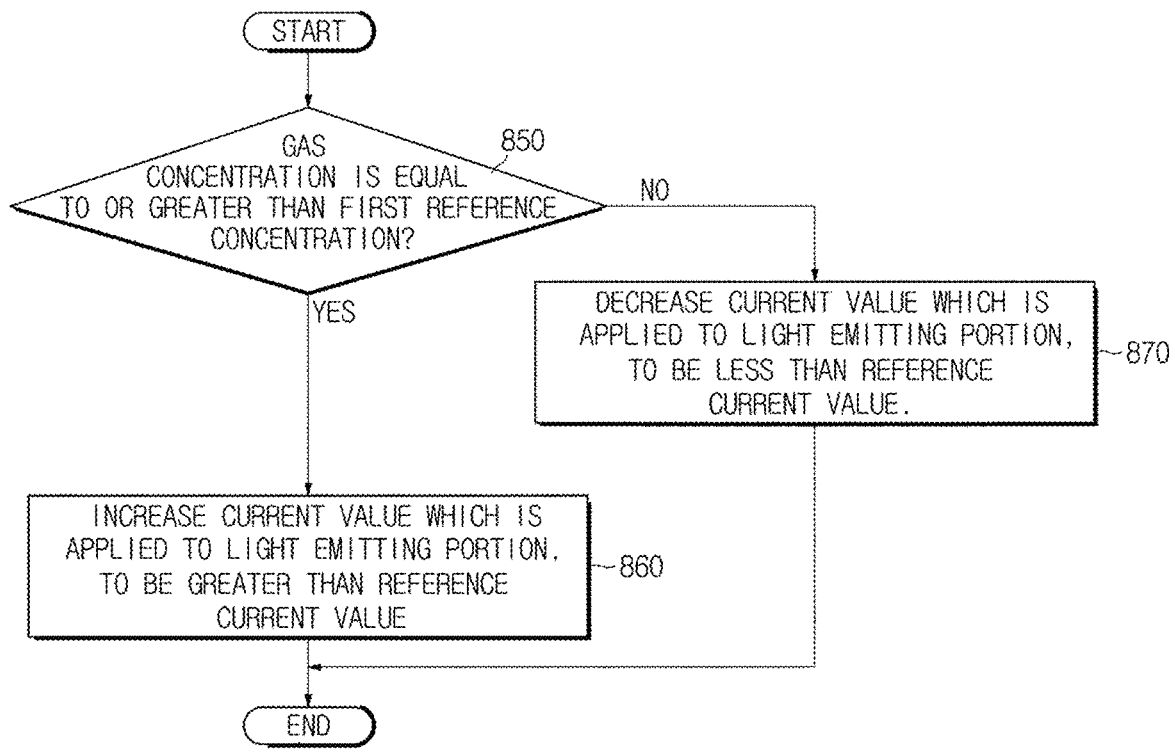

Referring to FIG. 10, when the concentration of the gas is equal to or greater than the first reference concentration (850), the controller 700 may increase a current value, which is applied to the light emitting portion 310, to be greater than the reference current value (860), and when the concentration of the gas is less than the first reference concentration, the controller 700 may decrease a current value, which is applied to the light emitting portion 310, to be less than the reference current value (870).

For example, when the concentration of formaldehyde detected by the gas sensor 710 is equal to or greater than the first reference concentration, the controller 700 may increase the current value applied to the light emitting portion 310. That is, when the concentration of formaldehyde is equal to greater than the first reference concentration, the controller 700 may determine that a stronger air purification performance is required, and thus the controller 700 may apply a current value, which is increased higher than the reference current value corresponding to the first reference concentration, so that the intensity of ultraviolet light irradiated to the photocatalytic filter 400 is increased.

When the detected concentration of formaldehyde is reduced less than the first reference concentration, the controller 700 may determine that a situation, in which the strong air purification performance is required, is released, and the controller 700 may apply a current value, which is reduced less than the reference current value corresponding to the first reference concentration, so that the intensity of ultraviolet light irradiated to the photocatalytic filter 400 is reduced.

Figure 11:
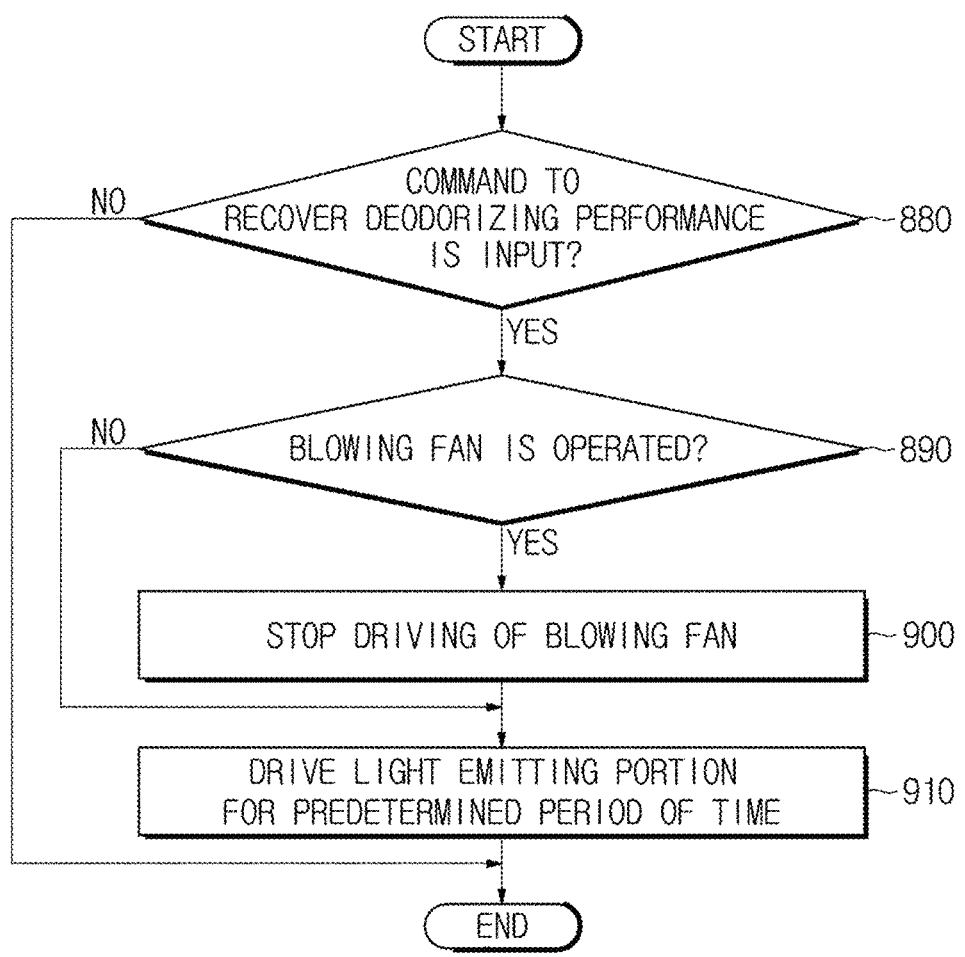

Referring to FIG. 11, when the command to recover the deodorizing performance is input (880), the controller 700 may determine whether the blowing fan 100 is operated or not (890), and when the blowing fan 100 is operated, the controller 700 may stop the drive of the blowing fan 100 (900), and operate the light emitting portion 310 for a predetermined period of time (910).

When the command to recover the deodorizing performance is input by a user, the controller 700 may determine whether the blowing fan 100 is operated or not. In a state in which the blowing fan 100 is operated, when ultraviolet light is irradiated to the photocatalytic filter 400, it may be similar with a case in which the deodorization and sterilization are performed by the photocatalytic filter 400. Therefore, the controller 700 may determine whether the blowing fan 100 is operated or not.

When the blowing fan 100 is operated, the controller 700 may stop the drive of the blowing fan 100, and operate the light emitting portion 310 for the predetermined period of time, so that ultraviolet light is irradiated to the photocatalytic filter 400. When the blowing fan 100 is not operated, the controller 700 may immediately operate the light emitting portion 310 for the predetermined period of time.

In a state in which the flow of the outside air by the blowing fan 100 is stopped, when ultraviolet light is irradiated to the photocatalytic filter 400, contaminants attached to the photocatalytic filter 400 may be decomposed or removed by the reaction of the photocatalyst with ultraviolet light, and thus the deodorizing and sterilizing performance of the photocatalytic filter 400 may be restored.

Figure 12:
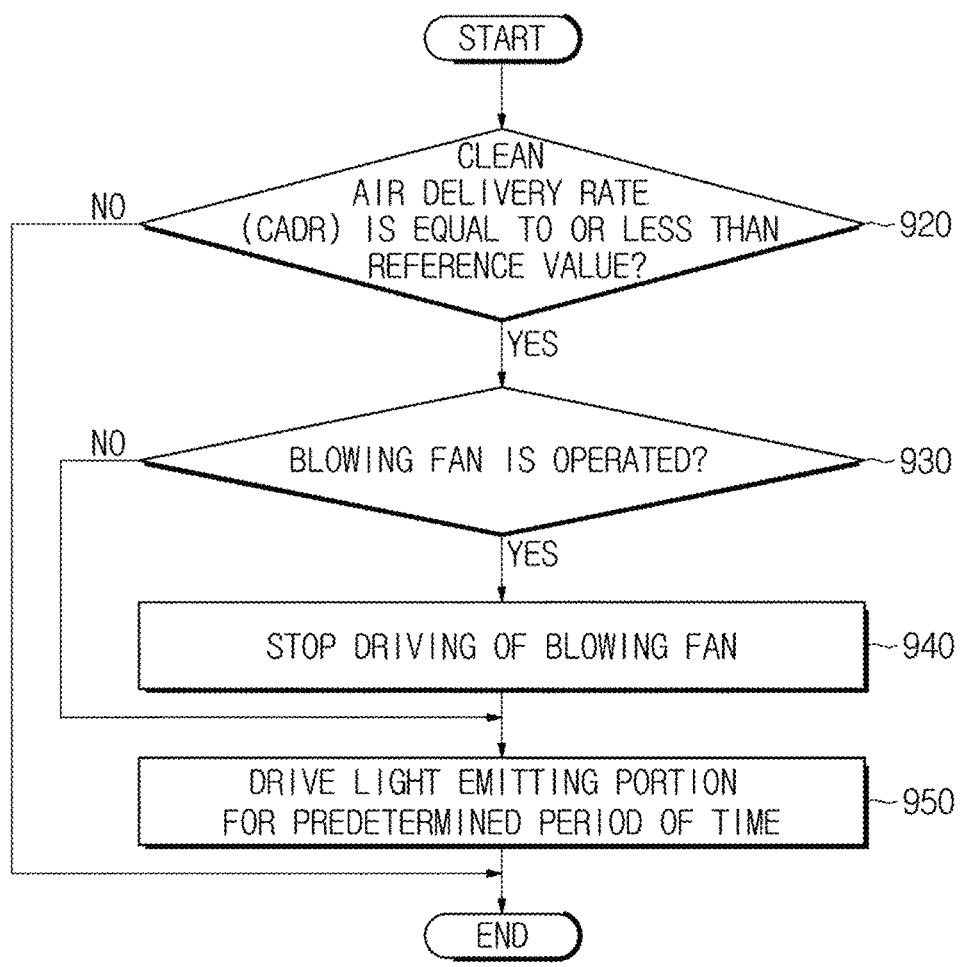

Referring to FIG. 12, when the clean air delivery rate (CADR) is equal to or less than the reference value (920), the controller 700 may determine whether the blowing fan 100 is operated or not (930), and when the blowing fan 100 is operated, the controller 700 may stop the drive of the blowing fan 100 (940), and operate the light emitting portion 310 for the predetermined period of time (950).

Although the deodorizing performance recovery command is not input via the input 720, the controller 700 may automatically perform the control for the deodorizing performance recovery when the amount of clean air is reduced equal or less than a reference value. In other words, when the clean air delivery rate (CADR) is reduced equal to or less than the reference value, the controller 700 may determine whether the blowing fan 100 is operated or not. When the blowing fan 100 is operated, the controller 700 may stop the drive of the blowing fan 100, and operate the light emitting portion 310 for the predetermined period of time, so that ultraviolet light is irradiated to the photocatalytic filter 400 for the predetermined period of time. When the blowing fan 100 is not operated, the controller 700 may immediately operate the light emitting portion 310 for the predetermined period of time.

When the clean air delivery rate (CADR) is reduced equal to or less than the reference value, the controller 700 may determine whether the blowing fan 100 is operated or not. In a state in which the blowing fan 100 is operated, when ultraviolet light is irradiated to the photocatalytic filter 400, it may be similar with a case in which the deodorization and sterilization are performed by the photocatalytic filter 400. Therefore, the controller 700 may determine whether the blowing fan 100 is operated or not.

When the blowing fan 100 is operated, the controller 700 may stop the drive of the blowing fan 100, and operate the light emitting portion 310 for the predetermined period of time, so that ultraviolet light is irradiated to the photocatalytic filter 400. When the blowing fan 100 is not operated, the controller 700 may immediately operate the light emitting portion 310 for the predetermined period of time. A current value, which is applied to the light emitting portion 310 when the light emitting portion 310 is operated for the predetermined period of time, may be pre-determined and the controller 700 may apply the predetermined and stored current value to the light emitting portion 310.

Figure 13:
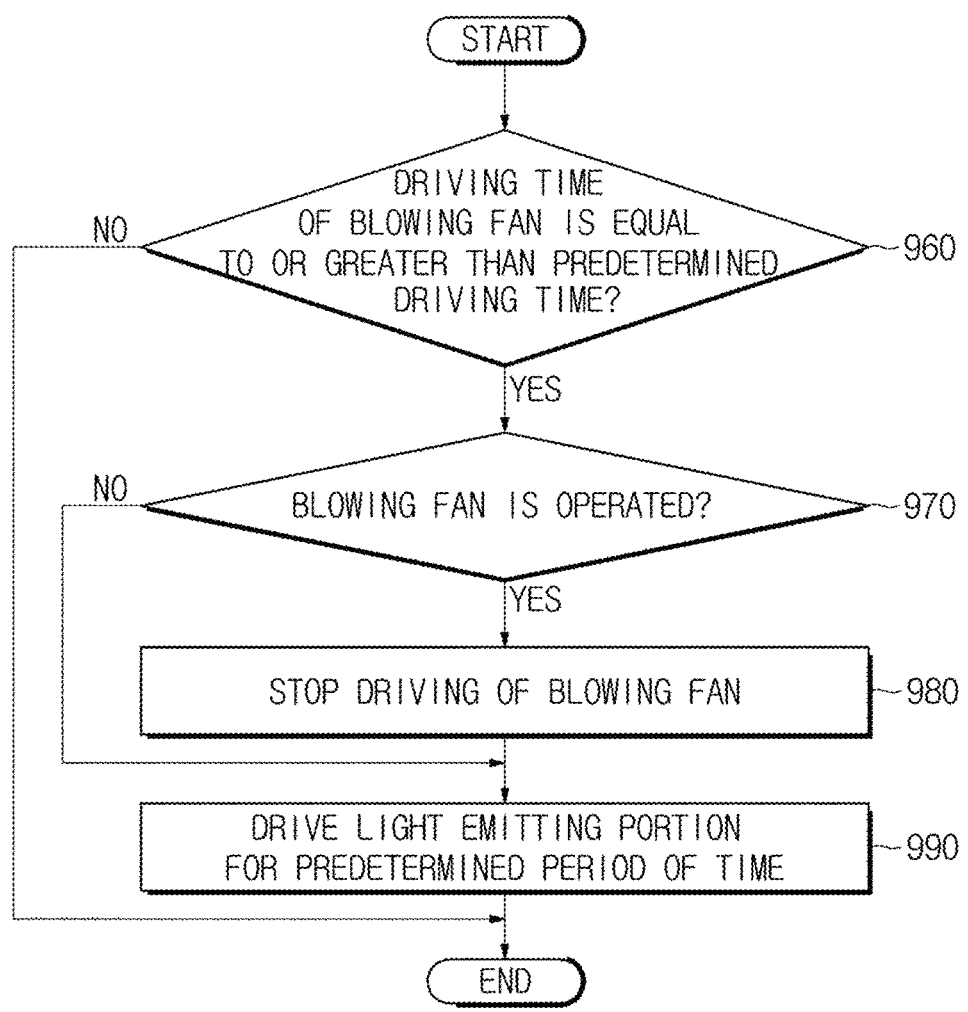

Referring to FIG. 13, when the driving time of the blowing fan 100 is equal to or greater than a predetermined driving time (960), the controller 700 may determine whether the blowing fan 100 is operated or not (970), and when the blowing fan 100 is operated, the controller 700 may stop the drive of the blowing fan 100 (980), and operate the light emitting portion 310 for the predetermined period of time (990).

Although the deodorizing performance recovery command is not input via the above mentioned input 720, the controller 700 may automatically perform the control for the deodorizing performance recovery when the driving time of the blowing fan 100 is equal to or greater than the predetermined driving time. The driving time of the blowing fan 100 may be a cumulative driving time.

In other words, when the cumulative driving time of the controller 700 is equal to or greater than the predetermined drive time, e.g., 10 hours, the controller 700 may determine whether the blowing fan 100 is operated. The cumulative driving time may exceed 10 hours during the blowing fan 100 is operated, or the drive of the blowing fan 100 may be stopped since the electronic apparatus is stopped shortly after the cumulative driving time exceeds 10 hours, and thus the controller 700 may determine whether the blowing fan 100 is operated or not.

When the blowing fan 100 is operated, the controller 700 may stop the drive of the blowing fan 100, and operate the light emitting portion 310 for the predetermined period of time, so that ultraviolet light is irradiated to the photocatalytic filter 400. When the blowing fan 100 is not operated, the controller 700 may immediately operate the light emitting portion 310 for the predetermined period of time. A current value, which is applied to the light emitting portion 310 when the light emitting portion 310 is operated for the predetermined period of time, may be pre-determined and the controller 700 may apply the predetermined and stored current value to the light emitting portion 310.

Figure 14:
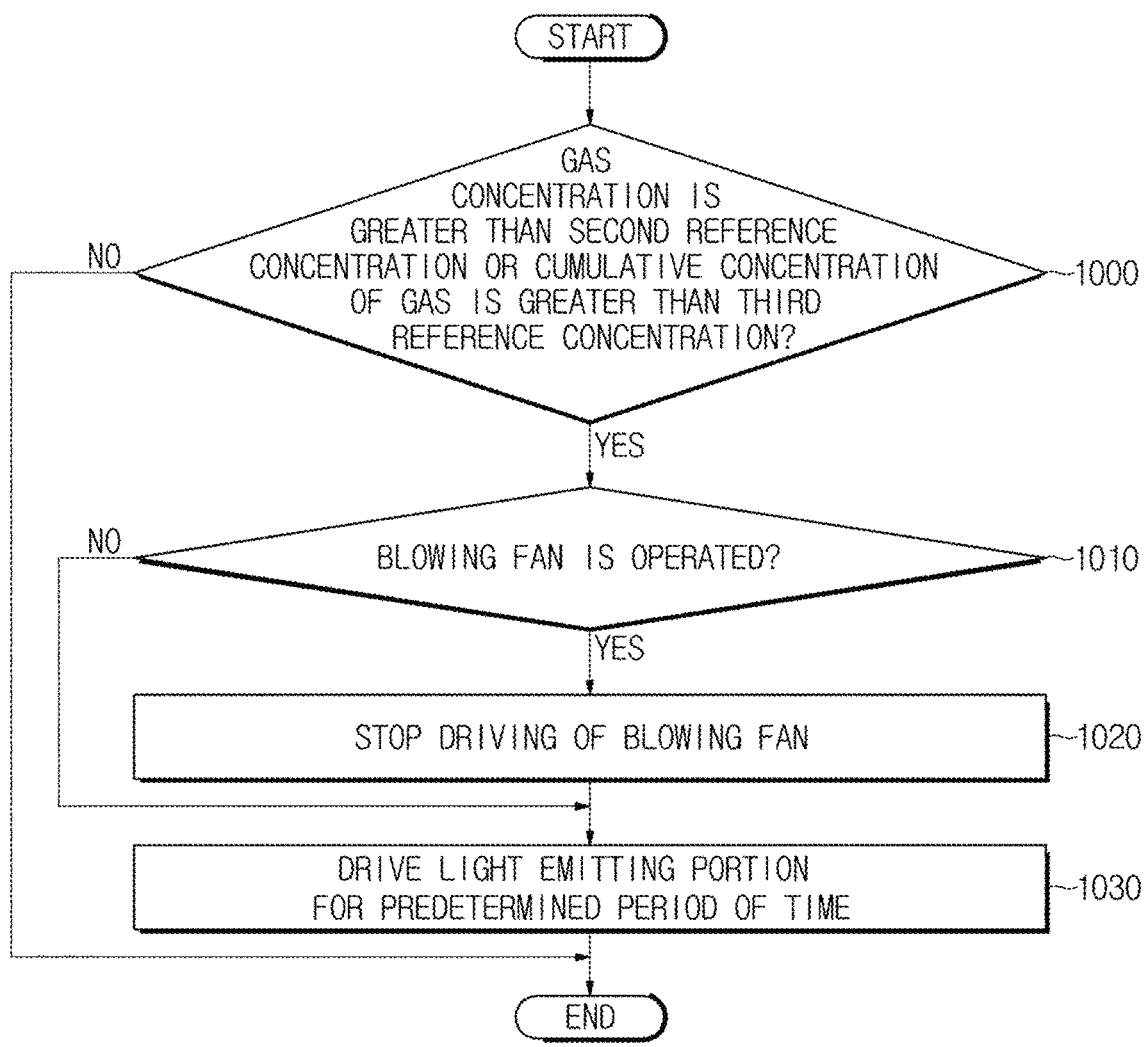

Referring to FIG. 14, when the concentration of the gas is greater than the second reference concentration or when the cumulative concentration of the gas is greater than the third reference concentration (1000), the controller 700 may determine whether the blowing fan 100 is operated or not (1010), and when the blowing fan 100 is operated, the controller 700 may stop the drive of the blowing fan 100 (1020), and operate the light emitting portion 310 for the predetermined period of time (1030).

Although the deodorizing performance recovery command is not input via the input 720, the controller 700 may automatically perform the control for the deodorizing performance recovery when the concentration of the certain gas detected by the gas sensor 710 is higher than the second reference concentration or when the cumulative concentration of the certain gas detected by the gas sensor 710 is higher than the third reference concentration. The above mentioned first to third reference concentration corresponding to a reference value, which is compared with the concentration of the certain gas, may be pre-stored in the storage 130 or the memory.

For example, when the concentration of formaldehyde detected by the gas sensor 710 is equal to or higher than the second reference concentration or when the cumulative concentration of formaldehyde detected by the gas sensor 710 is equal to or higher than the third reference concentration, the controller 700 may determine whether the blowing fan 100 is operated or not.

When the blowing fan 100 is operated, the controller 700 may stop the drive of the blowing fan 100, and operate the light emitting portion 310 for the predetermined period of time, so that ultraviolet light is irradiated to the photocatalytic filter 400. When the blowing fan 100 is not operated, the controller 700 may immediately operate the light emitting portion 310 for the predetermined period of time. A current value, which is applied to the light emitting portion 310 when the light emitting portion 310 is operated for the predetermined period of time, may be pre-determined and the controller 700 may apply the predetermined and stored current value to the light emitting portion 310.

As is apparent from the above description, it may be possible to provide the electronic apparatus capable of adjusting the air purification performance of the photocatalytic filter according to the air volume of the blowing fan and the variation of the certain gas concentration.

It may be possible to provide the electronic apparatus having the function of the deodorizing performance recovery of the photocatalytic filter.

Although a few embodiments of the present disclosure have been shown and described, it would be appreciated by those skilled in the art that changes may be made in these embodiments without departing from the principles and spirit of the disclosure, the scope of which is defined in the claims and their equivalents.

What is claimed is:

1. An electronic apparatus comprising:
   a blowing fan;
   a filter apparatus configured to purify air introduced by the blowing fan, the filter apparatus comprising a light emitting module outputting ultraviolet light, a photocatalytic filter provided to face a light emitting portion of the light emitting module, and a support frame configured to support the light emitting module and the photocatalytic filter to be apart from each other by a predetermined distance; and
   a controller configured to determine an air volume of the blowing fan when the blowing fan is operated, adjust a current applied to the light emitting module to output ultraviolet light based on a change in the air volume of the blowing fan, and operate the light emitting module for a predetermined period of time so that ultraviolet light is irradiated to the photocatalytic filter when the blowing fan is stopped operating.

2. The electronic apparatus of claim 1, wherein when the air volume of the blowing fan is changed from a first mode to a second mode, which is stronger than the first mode, the controller is configured to increase a first current value, applied to the light emitting portion, to a second current value corresponding to the second mode, which is greater than the first current value corresponding to the first mode.

3. The electronic apparatus of claim 1, wherein when the air volume of the blowing fan is changed from a second mode to a first mode, which is weaker than the second mode, the controller is configured to decrease a second current value applied to the light emitting portion, to a first current value corresponding to the first mode, which is less than a second current value corresponding to the second mode.

4. The electronic apparatus of claim 1, further comprising:
   a gas sensor configured to detect a concentration of a predetermined gas contained in the air introduced by the blowing fan.

5. The electronic apparatus of claim 4, wherein the controller is configured to adjust the current applied to the light emitting portion based on the concentration of the predetermined gas detected by the gas sensor.

6. The electronic apparatus of claim 4, wherein when the concentration of the predetermined gas detected by the gas sensor is greater than a first reference concentration, the controller is configured to increase the current value applied to the light emitting portion, to be greater than a reference current value based on the first reference concentration.

7. The electronic apparatus of claim 4, wherein when the concentration of the predetermined gas detected by the gas sensor is less than a first reference concentration, the controller is configured to decrease the current value applied to the light emitting portion, to be less than a reference current value based on the first reference concentration.

8. The electronic apparatus of claim 4, wherein in a state in which the concentration of the predetermined gas detected by the gas sensor is greater than a second reference concentration or a cumulative concentration of the predetermined gas is greater than a third reference concentration, when the blowing fan is operated, the controller is configured to stop the blowing fan and to operate the light emitting portion for a predetermined period of time so that ultraviolet light is irradiated to the photocatalytic filter.

9. The electronic apparatus of claim 1, wherein in a state in which a command to recover a deodorizing performance is input, when the blowing fan is operated, the controller is configured to stop the blowing fan and to operate the light emitting portion for a predetermined period of time so that ultraviolet light is irradiated to the photocatalytic filter.

10. The electronic apparatus of claim 1, wherein when the blowing fan is stopped by the controller, the controller is configured to operate the light emitting portion for a predetermined period of time so that ultraviolet light is irradiated to the photocatalytic filter to recover a deodorizing performance of the photocatalytic filter.

11. The electronic apparatus of claim 1, wherein in a state in which a clean air delivery rate (CADR) of the electronic apparatus reaches a reference value, when the blowing fan is operated, the controller is configured to stop the blowing fan and operates the light emitting portion for a predetermined period of time so that ultraviolet light is irradiated to the photocatalytic filter to recover a deodorizing performance of the photocatalytic filter.

12. The electronic apparatus of claim 1, wherein when the blowing fan is operated for a predetermined driving time or longer, the controller is configured to stop the blowing fan and to operate the light emitting portion for a predetermined period of time so that ultraviolet light is irradiated to the photocatalytic filter to recover a deodorizing performance of the photocatalytic filter.

13. The electronic apparatus of claim 1, wherein the photocatalytic filter comprises a base which a photocatalyst is applied thereto.

* * * * *